United States Patent [19]
Thornton et al.

[11] Patent Number: 5,104,395
[45] Date of Patent: Apr. 14, 1992

[54] AUTOMATIC HEMOSTATIC CLIP APPLICATOR

[75] Inventors: Curtis W. Thornton, Cary; Robert W. Mericle, Raleigh; Mark T. Everett, Cary; Robert S. Lynch, Durham, all of N.C.

[73] Assignee: Edward Weck Incorporated, Princeton, N.J.

[21] Appl. No.: 684,139

[22] Filed: Apr. 11, 1991

Related U.S. Application Data

[63] Continuation of Ser. No. 375,174, Jul. 3, 1989, abandoned.

[51] Int. Cl.⁵ .............................................. A61B 17/12
[52] U.S. Cl. .................................................... 606/143
[58] Field of Search ................................ 606/143, 142

[56] References Cited

U.S. PATENT DOCUMENTS

| | | |
|---|---|---|
| 2,968,041 | 1/1961 | Skold . |
| 3,777,538 | 12/1973 | Weatherly et al. . |
| 4,152,920 | 5/1979 | Green . |
| 4,166,466 | 9/1979 | Jarvik . |
| 4,226,242 | 10/1980 | Jarvik . |
| 4,242,902 | 1/1981 | Green . |
| 4,299,224 | 11/1981 | Noiles . |
| 4,316,468 | 2/1982 | Klieman et al. . |
| 4,325,376 | 4/1982 | Klieman et al. . |
| 4,372,316 | 2/1983 | Blake, III et al. . |
| 4,412,539 | 11/1983 | Jarvik . |
| 4,425,915 | 1/1984 | Ivanov . |
| 4,430,997 | 2/1984 | DiGiovanni et al. . |
| 4,448,193 | 5/1984 | Ivanov . |
| 4,450,839 | 5/1984 | Transue . |
| 4,471,780 | 9/1984 | Menges et al. . |
| 4,480,640 | 11/1984 | Becht .................... 606/143 |
| 4,509,518 | 4/1985 | McGarry et al. . |
| 4,522,207 | 6/1985 | Klieman et al. . |
| 4,534,351 | 8/1985 | Rothfuss et al. ........... 606/143 |
| 4,549,544 | 10/1985 | Favaron .................. 606/143 |
| 4,557,263 | 12/1985 | Green . |
| 4,572,183 | 2/1986 | Juska . |
| 4,576,166 | 3/1986 | Montgomery et al. . |
| 4,598,711 | 7/1986 | Deniega . |
| 4,611,595 | 9/1986 | Klieman et al. . |
| 4,616,650 | 10/1986 | Green et al. . |
| 4,646,740 | 3/1987 | Peters et al. ............. 606/143 |
| 4,712,549 | 12/1987 | Peters et al. . |

Primary Examiner—Michael H. Thaler
Attorney, Agent, or Firm—Gene Warzecha

[57] ABSTRACT

An automatic hemostatic clip applicator is disclosed wherein the jaws, cartridge assembly and jaw housing move together in a single direction to crimp a clip resulting in a perception of little or no motion by the jaws when the applicator is activated. Camming surfaces in the jaws are brought into contact with camming surfaces on the distal end of the stationary body of the applicator as the jaws are moved proximally.

11 Claims, 7 Drawing Sheets

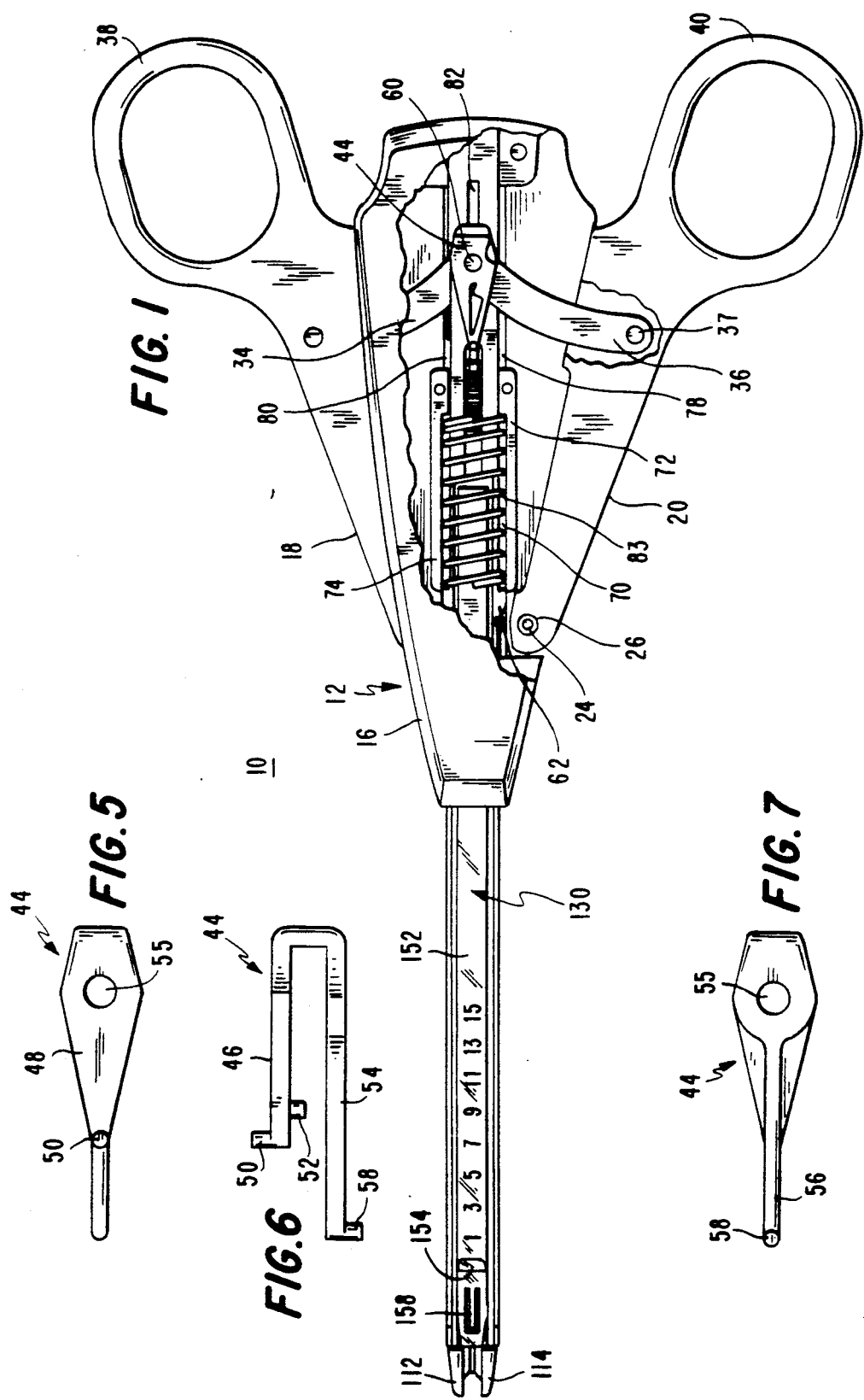

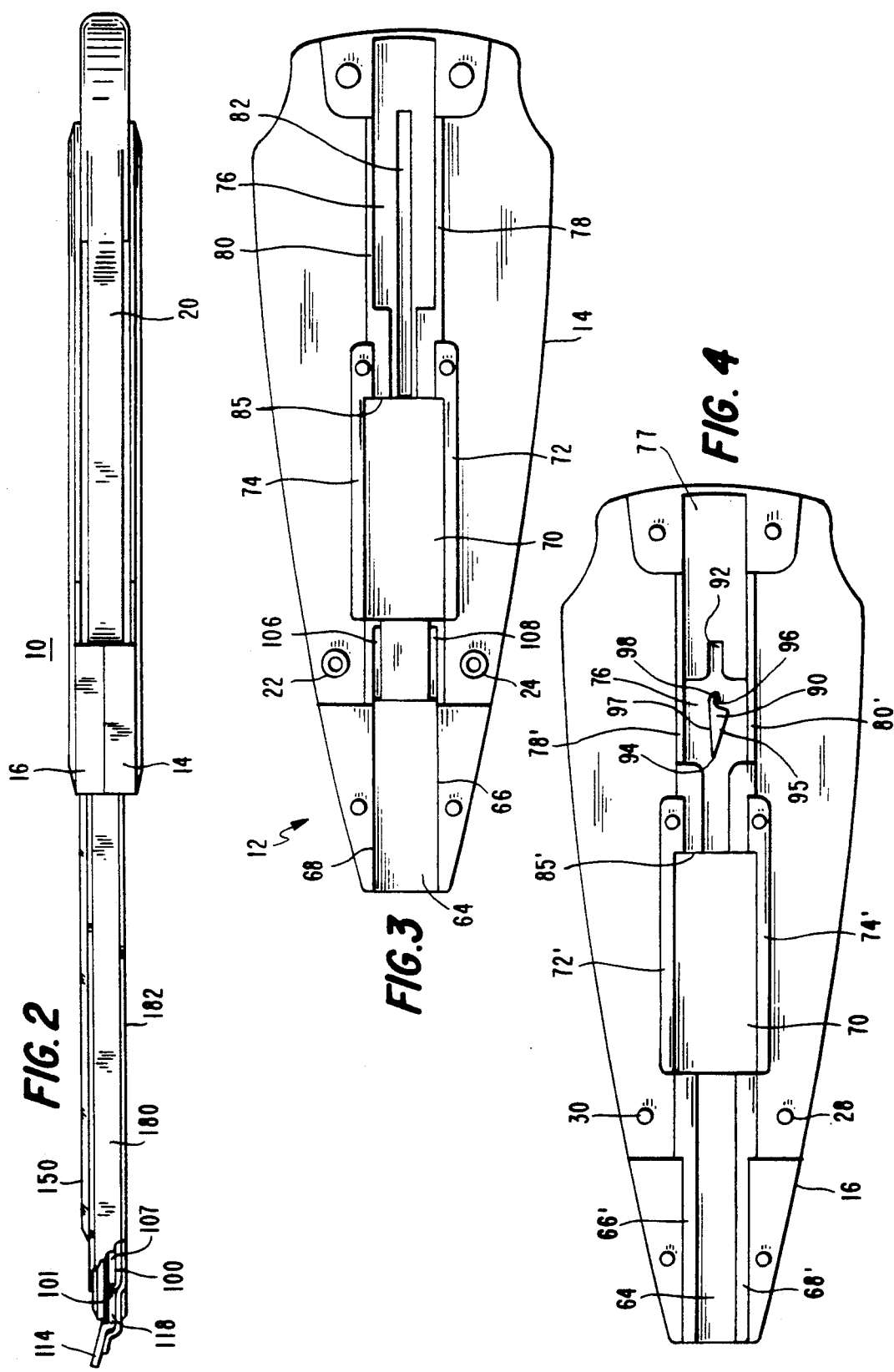

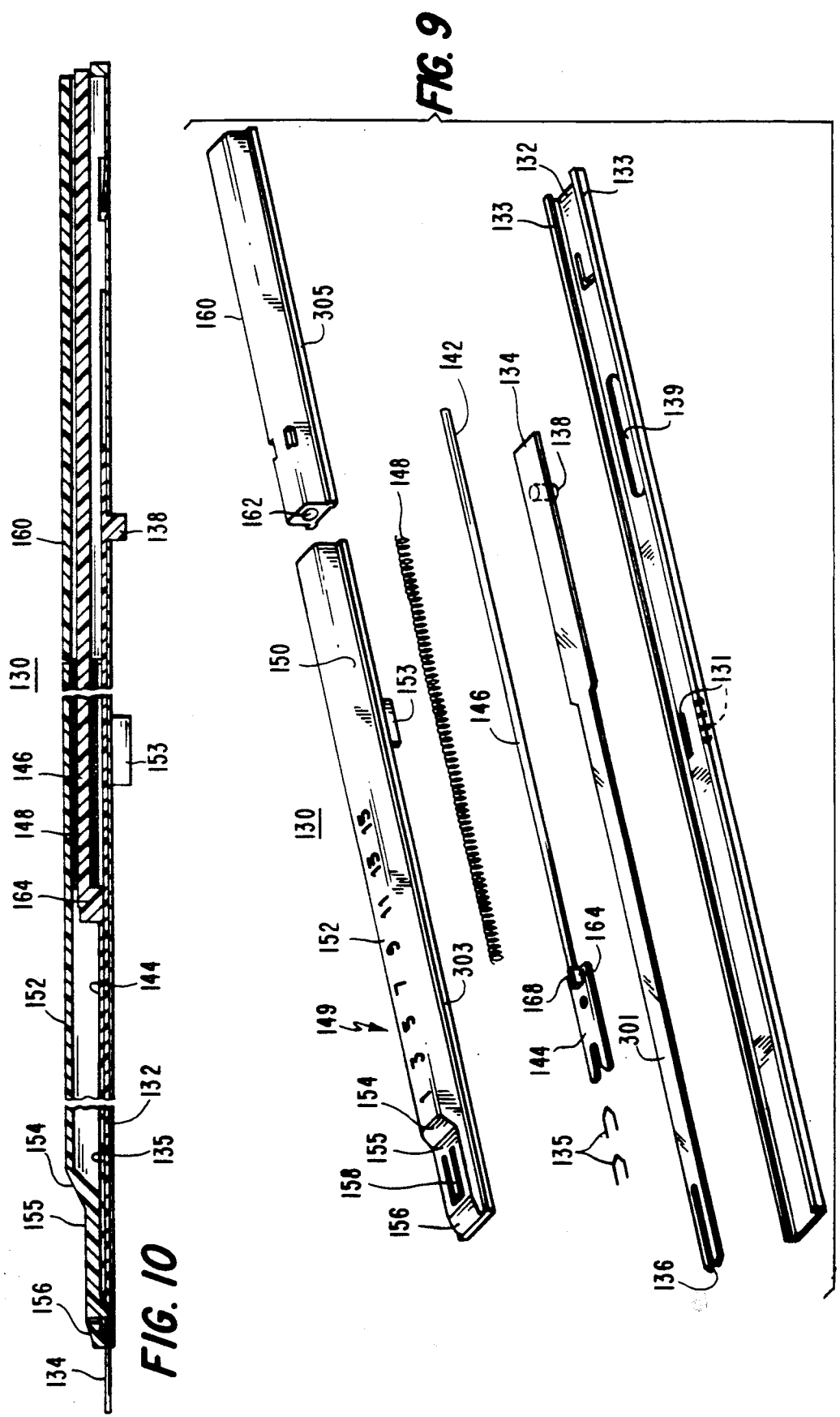

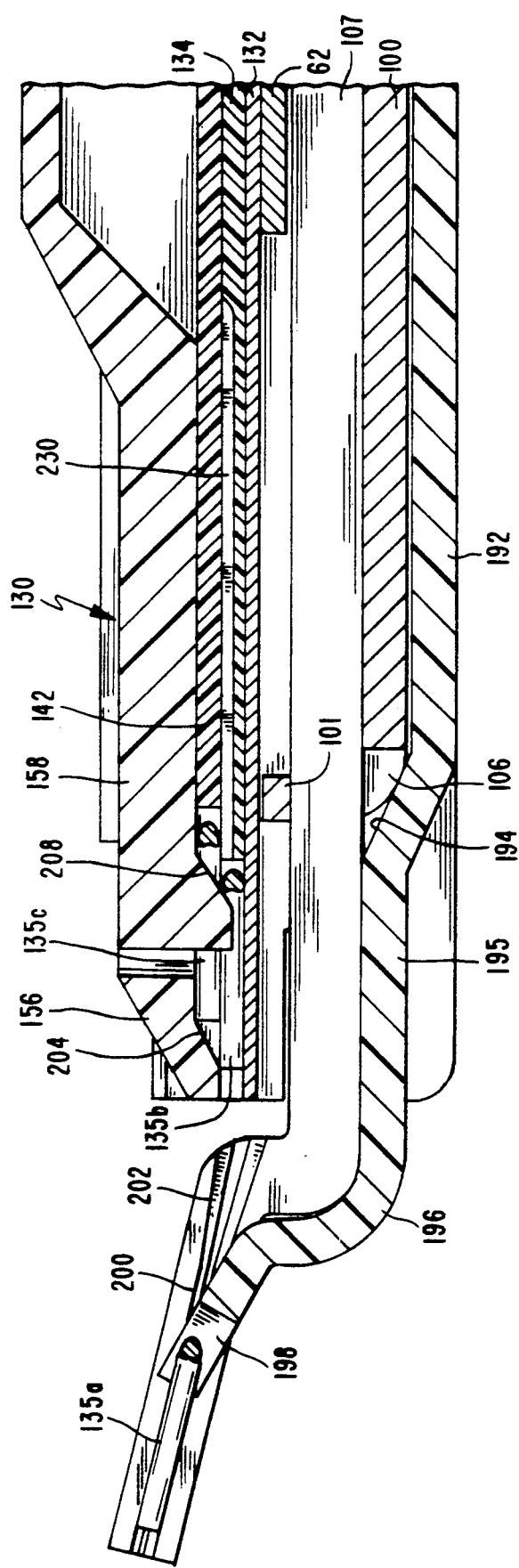

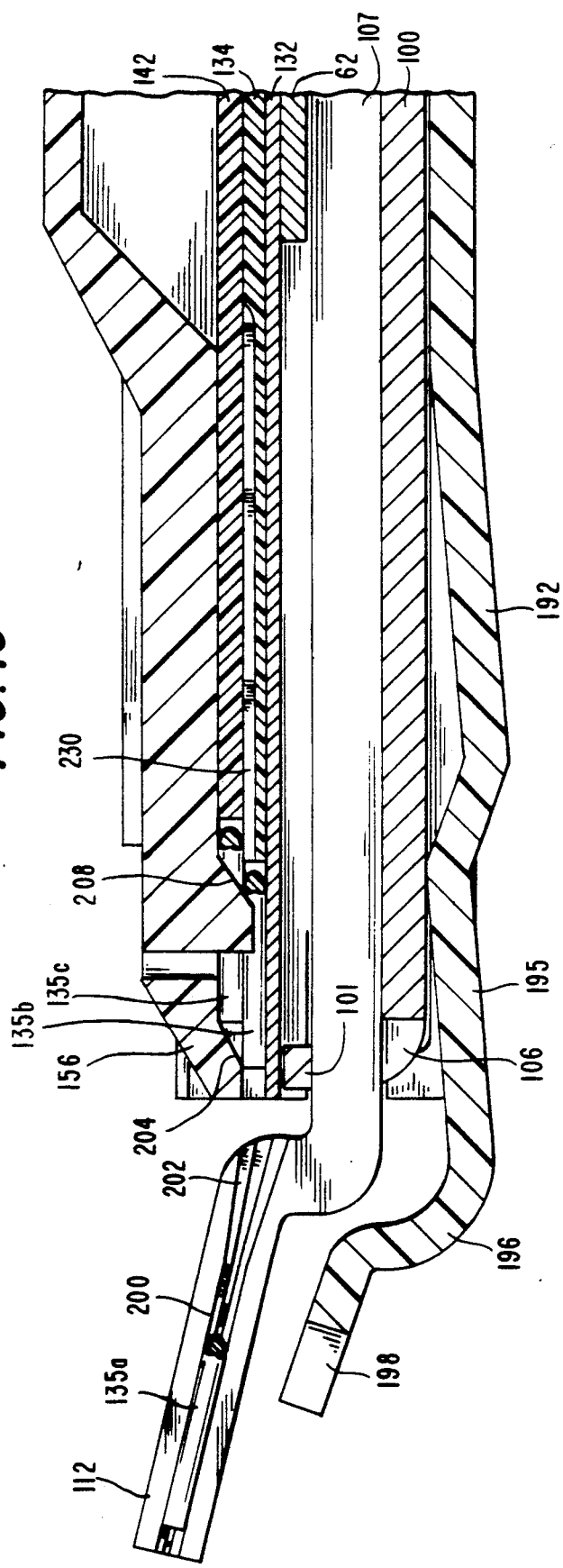

AUTOMATIC HEMOSTATIC CLIP APPLICATOR

This is a continuation application of application Ser. No. 07/375,174 filed July 3, 1989 now abandoned.

BACKGROUND OF THE INVENTION

This invention relates to instruments for applying surgical clips to body tissue, more particularly to instruments which at the same time store, dispense and crimp such clips.

Surgical or hemostatic clips are used to clamp off blood vessels or other tissue which are cut during surgery. Each clip has two legs which are placed about the tissue to be clamped. The clip applying instrument is used to squeeze the legs together to seal off the tissue. An operation may entail the use of twenty or more clips. Initially each clip to be applied had to be picked up by the jaws of the applying instrument from a separate clip cartridge or dispenser prior to each use. Later instruments, some of them disposable, incorporated the clip dispenser as part of the instrument. See, for example, U.S. Pat. No. 4,452,376, U.S. Pat. No. 4,509,518 and U.S. Pat. No. 4,712,549, the latter being assigned to the assignee of this invention.

In addition to the dispenser, the automatic dispensing instruments described above generally include a pair of jaws for receiving, holding and crimping a single clip at a time and a feeding means for feeding a clip from the dispenser to the jaws. The jaws and feeder are activated in proper sequence by an activating means usually including a pair of handles coupled mechanically to the feeder and jaws.

With instruments of this type, it is very important that the feel of the instrument is right for the surgeon, including the placement of the handles, smoothness of operation and the surgeon's perception of the jaws about the tissue to be crimped during operation. This can include several factors including good visibility and the perception that there is no relative movement between the jaws and the body of the instrument. For disposable instruments, cost is a factor but not at the expense of reliability. Improvements are constantly being sought in this type of instrument to obtain less cost, more simplicity, greater feel and high reliability.

It is an object of the present invention to provide all of the above in an automatic hemostatic clip applicator.

SUMMARY OF THE INVENTION

An automatic hemostatic clip applicator is provided which includes a body having a dispensing and crimping portion, which further includes: a pair of jaws for receiving, holding and crimping a clip; means for holding a plurality of clips; a dispensing means for dispensing a single clip one at a time; and a feeding means for delivering the clip to the jaw means. The applicator further includes an activating and sequencing portion for activating the jaws and feeding means in proper sequence, the activating and sequencing means including a lever means for movement between a first open position and a second closed position.

The jaws are located near the distal end of the body portion of the applicator and the jaws are moved relative to the distal body portion to cause camming surfaces associated with the jaws and body portion to engage to close the jaws. The means for holding a plurality of clips and the dispensing means move with the jaws so that there is no relative movement among them.

A single driver element is provided as part of the activating and sequencing means. The driver element is coupled to the feeding means and the jaws, and movement of the driver element in one direction activates the feeding means and jaws in proper sequence. Preferably, that direction is in the proximal direction of the instrument away from the location of the jaws.

A clip stop means is provided for holding the clip to be crimped in the jaws when the feeder is retracted from the jaws but before the clip is crimped by the jaws. In the preferred embodiment, the clip stop comprises a flexible pawl member which extends from the distal end of the jaw housing. The jaw housing is coupled to the means for storing a plurality of clips and the dispensing means and moves with the jaws.

The activating and sequencing means activates the feeder to move a clip into the jaws as the lever means is returned from the second closed position to the first open position. Means are provided for preventing feeding of another clip into the jaws until after the lever means has been moved into the second closed position. The means comprises a cam track in the body housing and a cam track follower coupled to the lever means.

In one aspect of the invention a cartridge subassembly is provided which includes a means for holding a plurality of clips, a dispensing means for dispensing a clip into a feeding path, a feeding means for moving a clip into the jaws. The cartridge assembly further includes a transparent cartridge tip through which the clip and a pusher for the clip are visible. Indicia are provided on the cartridge top and on the pusher for indicating how many clips are left in the cartridge.

BRIEF DESCRIPTION OF THE DRAWINGS

FIG. 1 is a plan view, partially broken away, of the instrument of the present invention for storing, dispensing and applying hemostatic clips.

FIG. 2 is a side plan view of the instrument as shown in FIG. 1.

FIG. 3 is an enlarged plan view of the inside of the bottom housing of the instrument of FIG. 1.

FIG. 4 is an enlarged plan view of the inside of the top housing of the instrument of FIG. 1.

FIG. 5 is an enlarged top plan view of a ratchet yoke of the instrument of FIG. 1.

FIG. 6 is an elevational plan view of the yoke of FIG. 5.

FIG. 7 is a bottom plan view of the yoke of FIG. 5.

FIG. 9 is an enlarged top plan view of a cartridge assembly portion of the portion shown in FIG. 8.

FIG. 10 is an enlarged, elevational, cross-sectional view of the cartridge assembly portion of FIG. 9.

FIG. 12 is an elevational, cross-section of the portion of the instrument shown in FIG. 11 in the pre-cock position.

FIG. 13 is an elevational, cross-section of the portion of the instrument shown in FIG. 11 in a fully activated position.

DETAILED DESCRIPTION OF THE DRAWINGS

Figure 8:
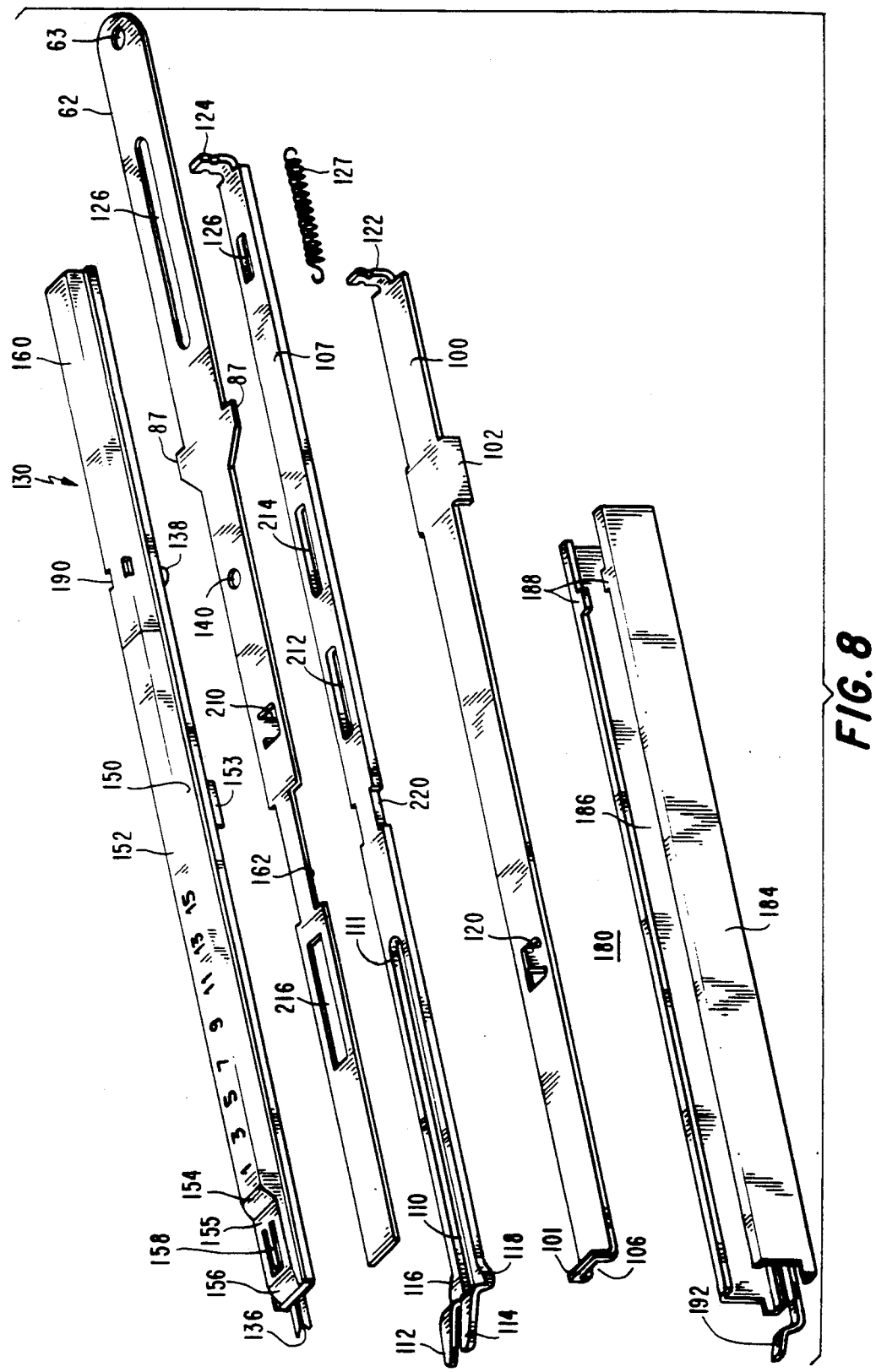
FIG. 8 is an exploded view of the components of a portion of the instrument of FIG. 1 including the dispensing and crimping portion.

The present invention hemostatic clip applier designated generally 10 in the drawings comprises a housing 12 having bottom and top portions 14 and 16, respectively; and a pair of identical ring handles 18 and 20 which are pivotally attached to the housing 12. The housing and ring handles are preferably made of a moldable plastic such as polycarbonate but could be metal or any other suitable material. A pair of posts 22 and 24 rise up from the distal end portion of the bottom portion, one for each ring handle. The post passes through a hole, such as hole 26 at the distal end of the ring handle 20. The mating top portion 16 has a pair of pins 28, 30 which are adapted to be inserted into holes in the posts 22 and 24, respectively.

The ring handles 18 and 20 are also coupled to the housing 12 by a pair of identical curved link members 34 and 36, respectively. Each link member at one end is coupled to the medial portion of each ring handle by a pin 37 just distally of the ring portions 38 and 40. The other end of each link member is coupled to a ratchet yoke 44.

The ratchet yoke 44 is shown in more detail in FIGS. 5-7 and comprises a generally U-shaped member having a top leg 46 which forms a V-shaped distal portion 48 with a first post 50 extending outwardly from the top leg 46 at the distal tip and a second post 52 located proximally of post 50 and extending interiorly toward the bottom leg 54. The bottom leg has an elongated portion 56 extending distally with a post 58 extending outwardly from the leg 54 at the leg distal tip. The top and bottom legs each have a hole 55 aligned with each other to receive a pin. The opposite ends of link members 34 and 36 are pivotally connected to the ratchet yoke 44 by the pin 60 which is press fit into the holes 55 of the yoke. A driver link 62 which will be described in more detail later is also coupled by the pin 60 to the yoke 44. The yoke is a plastic part and is resilient and flexible. The top leg can be twisted out of alignment with the bottom leg but will return into alignment with the bottom leg when the twisting force is removed.

Referring to FIG. 3, housing 12 has a longitudinal track defined therethrough generally along its longitudinal centerline. Looking first at the bottom portion, the track has a number of portions including the distal most portion 64 defined by parallel and spaced apart walls 66 and 68; a center portion 70 of somewhat larger width defined by parallel walls 72 and 74; and a proximal portion 76 defined by walls 78 and 80. The proximal portion includes a longitudinal slot 82 in the bottom of the track lying along the housing and instrument centerline.

The top portion 16 has a similar wall structure to help define the longitudinal track having distal mating walls 66' and 68'; intermediate walls 72' and 74' which mate with walls 72 and 74; and proximal spaced apart walls 78' and 80'. Walls 78' and 80' do not come in contact with walls 78 and 80 to allow for passing of the link members 34 and 36 to extend from the ring handles to the ratchet yoke.

The center portion 70 of the track has a larger width to accommodate a relatively large compression spring 83. The driver element 62 passes through the spring. The spring is captured lengthwise in the track between the proximal end walls 85, 85' of the center portion 70 of the track where they narrow to end the center portion and a pair of wings 87 (FIG. 8) on opposite sides of the driver link 62. The driver link, whose function will be described later, extends through the distal portion of the track to emerge from the housing 12 and extend distally therefrom. The compression spring 83 biases the ring handles open; since it attempts to push the driver link 62 distally. The driver link is proximally coupled through hole 63 to the pin 60 in the ratchet yoke 44 which in turn is coupled to the ring handles by link members 34 and 36.

A raised cam track 90 in the shape shown in FIG. 4 lies along the longitudinal centerline of the floor of the proximal portion 76 of the track of the top portion. The floor of a proximal portion of the track portion 7 is raised slightly at 77 proximally of the cam track 90 and includes a slot 92 lying along the centerline of the raised floor having its proximal end closed and its distal end open.

The cam track comprises a generally triangular shape having a rounded base opposite a distally located V-shaped apex 94 formed by straight sides 95 and 97. The apex lies on one side of the centerline of the cam proximal track portion while the rounded end has a curved cut out 96 forming a curved finger 98. The curved cut out 96 lies intermediate the tip of the curved finger 98 and the apex 94. The curved finger lies nearby the opening to the slot 92 and extends past the centerline of the proximal track portion on a side of the centerline opposite the apex 94.

When +h=top portion 16 is connected to the bottom portion 14 (posts with centerholes extend from the walls 66, 68; 72, 74; and from the proximal end of the bottom portion to receive mating posts from the walls of the track of the top portion), the ratchet yoke 44 is captured between them but is enabled to translate back and forth in the proximal track portion 76 as the ring handles are squeezed together against the action of compression spring 83 or spread apart by the return action of the spring. The post 58 on bottom leg 54 always rides in the longitudinal slot 82 in the floor of the bottom portion 14. When the ring handles are fully spread apart the, post 50 is located distally of the apex 94 along the centerline of the proximal track portion brought there by the location of post 58 in the slot 82. As the ring handles are squeezed together, the post 50 engages the side 95 of cam track 90 on the same side of the cam track as cut out 96. The post will always engage the side 95 first since the apex 94 is not on the centerline but off to the opposite side of the centerline. As the ring handles continue to be squeezed together the post 50 rides along the side 95 forcing the top leg to twist slightly from the bottom leg until the post rests in the cut out 96. At this point the cam track prevents the compression spring, which is under partial compression, from returning the ring handles or driver link 62 to their initial quiescent position. This is the pre-cock position whose importance will become apparent later. Continued squeezing of the ring handles forces the post 50 out of the cut out past the tip of finger 98. Once past the finger 98, the post 50 returns to the longitudinal centerline of the proximal track portion because the post 58 on the bottom leg of the yoke 44 rides in the slot 82 and the top leg wants to return to alignment with the bottom leg. When the ring handles are fully squeezed together, the post 50 moves to the closed end of slot 92.

As the ring handles are gradually released, the compression spring will force the ring handles open pulling the yoke 44 forward in the proximal track portion until the post 50 engages the cam track on the convex surface of the finger portion 98 contiguous with straight surface 97. The post 50 crosses over to this side of the cam track because the post is on the centerline of the proximal track portion but the tip of the finger is on one side of the center line. When the ring handles have returned to their initial position so does the ratchet yoke 44 and the post 50.

Also attached to housing 12 is a flat elongated closure member 100 preferably made from stainless steel. It comprises a pair of rectangular tabs 102 on opposite sides of the member extending down from the plane of the closure member. The tabs 102 are adapted to be inserted into slots 106 and 108 in the bottom of bottom portion 14 between the distal and center track portions 64 and 70, respectively. The tabs 102 locate the closure member in the correct position relative to the housing 12.

The distal end 101 of the closure member 100 is bent up by approximately 90° through a rectangular hole 106 formed on the closure member at the distal end. The proximal end of an elongated largely flat jaw member 107 is passed through the vertical window formed by the bent distal end 101 and hole 106 of closure member 100 so that the jaw member 107 lies atop of the closure member 100.

The distal end of the jaw member is slotted along slot 110 from the distal end through a portion of the length of the jaw member along the centerline. The slot is open at the distal end separating opposing inner clip engaging surfaces of two opposed jaws 112 and 114. The bases of each of the jaws have curved outwardly extending camming surfaces 116 and 118. The jaws are bent upwardly from the plane of the jaw member, preferably at an angle of 13°, 22'. This provides better visibility for the surgeon when applying the clips. The camming surfaces 116 and 118 though still remain in the plane of the remainder of the jaw member behind the bent up portion of the jaws. The jaws with camming surfaces 116 and 118 are located distally of the window in the distal end 101 of the closure member 100. Camming surfaces 116 and 118 are provided with a profile which, upon the interaction of surfaces 116 and 118 with the sides of window 106, causes the jaws to close more quickly at the beginning of the crimping operation and more slowly at the end. The closure member 100 includes an upwardly extending center tab 120 which is adapted to fit within the slot 110 engaging the rear 111 of the slot 110 to prevent the jaw member 107 from translating distally relative to the closure member 100.

The proximal end of closure member 100 has an upwardly extending tab 122 while the proximal end of the jaw member 107 has an upwardly extending tab 124. The jaw member 107 is longer than the closure member 100 with the jaws 112 and 114 located distally of the window in distal end 101 of the closure member and having the tab 124 located proximally of the tab 122. Since the closure member is below the jaw member, tab 122 protrudes through jaw member 107 through opening 126 in the jaw member. A spring 127 connects the tabs and biases the jaw distally of the closure member forcing engagement of the rear 111 of slot 110 with closure member tab 120 until the spring force is overcome when the ring handles are squeezed together.

Along with the driver link 62, a medial portion of the closure member 100 and the jaw member 107 lie within the distal track portion 64. The proximal end of the closure member 100 and the jaw member 107 extend into the interior of the compression spring 83.

Referring now to FIG. 9, the instrument 10 comprises a pre-assembled clip cartridge designated generally 130 which stores a plurality of clips. The cartridge 130 includes a flat elongated cartridge bottom 132 which is in the shape of a tray with upstanding elongated sides 133 and laterally, interiorly directed flanges. The cartridge bottom is made of stainless steel and has a smooth interior bottom surface. A slot 131 is provided in the bottom of the medial portion of the bottom 132 next to a side wall. A plastic elongated feeder 134 sits on the bottom of the tray having a distal end 136 which is somewhat V-shaped to match up with the back of the V-shaped web portion of a hemostatic clip such as clips 135. At the proximal end portion of the feed 134 a post 138 extends downwardly from the center of the feeder and passes through an elongated opening 139 in the bottom of the cartridge bottom. The post 138 is adapted to pass through a hole 140 in the driver link 62. The hole 140 is just slightly larger than the post 138. As the driver link moves back and forth so does the feeder along the bottom of the cartridge bottom.

The hemostatic clips 135 are lined up on top of the flat feeder 134 in the region 301 with their legs pointed distally. The clips 135 all lie in a single plane parallel to the plane of the feeder 134. A plastic pusher 142 has a flat distal pusher end 144 with a V-shape adapted to engage the web of the rearmost clip in the cartridge. The pusher includes an elongated cylindrical rod 146 coupled to the pusher end 144 which extends proximally through a compression spring 148. The rod portion 146 is elevated slightly from the plane of the end 144 and the clips 135.

The cartridge assembly 130 includes an elongated plastic housing 149 having parallel side walls 150, a top 152, an open bottom and a two stage, tapered distal end. A tab 153 extends downwardly from one side wall and is positioned to pass through slot 131 in the cartridge bottom 132 and then ride along within timing slot 162 in driver link 62. The housing is preferably made of polycarbonate and has a fixed cross-section along most of its length from its proximal end until the two stage tapered distal end. The first taper 154 occurs spaced apart from the front end and reduces the height of the housing to about one-half. The top 155 of this portion remains flat until the second taper 156 is encountered at the distal end. The second taper 156 reduces the height of the housing to just larger than the thickness of a clip 135.

The cartridge is open at its reduced shaped distal end; at its proximal end it is closed except for a round aperture not shown. A flexible delta member 158 is formed in the flat top portion 155 separated from the rest of the top portion on its distal end and two sides and connected to portion 155 only at its rear. Its cross sectional shape and purpose will be discussed in more detail hereinafter.

The cartridge assembly 130 further comprises a cartridge plug 160. The cartridge plug 160 has a cross section along its length which is the same as the cross section of the proximal end of the cartridge top. Together the lengths of the housing 149 and plug 160 are substantially the same as the cartridge bottom 132. The plug 160 has an aperture 161 in its otherwise closed distal end which is aligned with the aperture in the proximal end of the housing 149.

As was mentioned earlier the cartridge is pre-assembled apart from the rest of the instrument. The feeder 134 is laid in the bottom 132 and hemostatic clips are lined up on top of the distal half of the feeder within the cartridge. The rod like portion 146 of pusher 142 is threaded through the compression spring 148 and the combination is placed through the open bottom into a longitudinal cylindrical bore in the housing 149. Where the flat distal portion 144 of the pusher meets the rod like portion 146, a step 164 is formed. Step 164 will engage the first tapered step 154 when all the clips 135 have been dispensed. Since the pusher 142 is larger than the housing 149, the rod portion 146 extends through the aperture in the proximal end of the housing, through the aperture 161 into a longitudinal cylindrical bore within plug 160. The spring 148, however, is too big to pass of through the aperture 161 in the distal end of the plug 160. The rod portion 146 of the pusher is pushed proximally into the plug 160 compressing the spring 148 to make room for the clips 135.

The cartridge housing has flanges 303 along its length at its bottom extending outwardly from the side walls 150. The housing is mounted on the bottom 132 with the flanges of bottom 132 overlaying the flanges 303 on the housing. The plug with flanges 305 is similarly mounted on the proximal end of the cartridge base 132. The completely assembled cartridge is shown in enlarged cross-section in FIG. 10.

Figure 11:
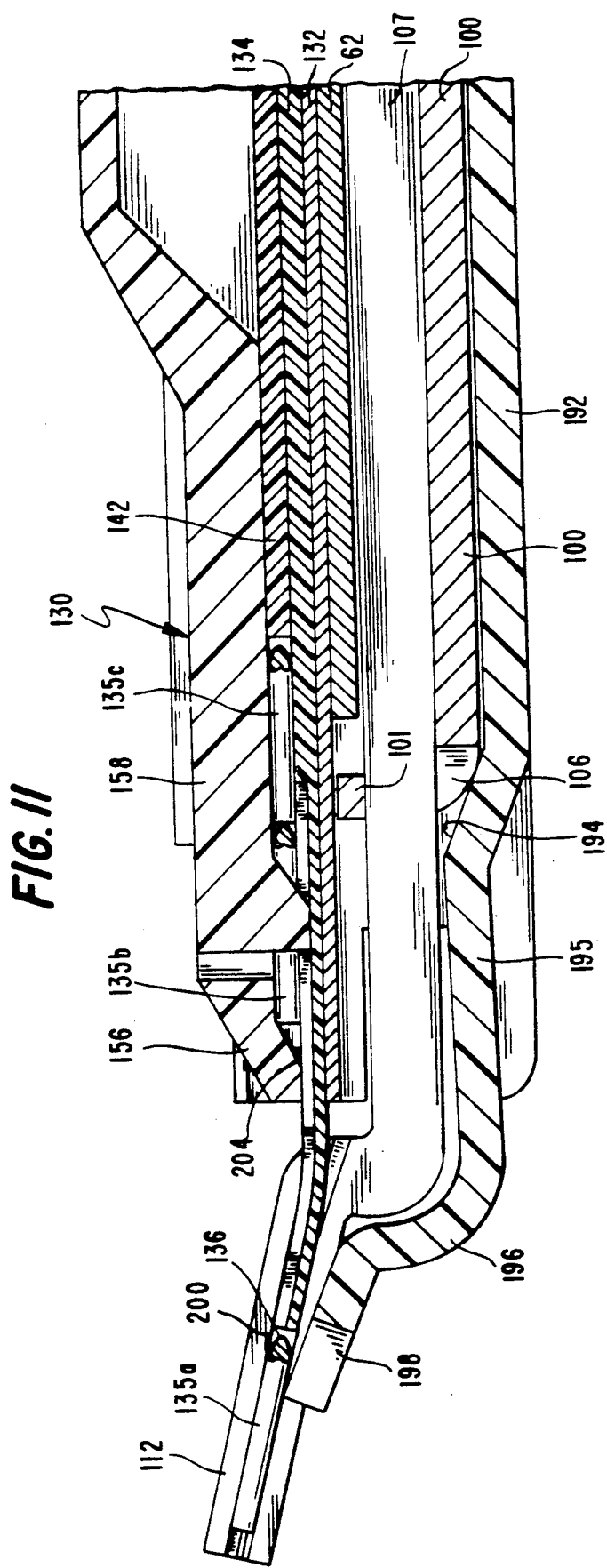
FIG. 11 is a greatly enlarged, elevational, cross-section of the distal end of the instrument of FIG. 1 in a quiescent position.

In the preferred embodiment the cartridge housing 149 is made of clear plastic with numbers painted on the top 152, such as the dark odd numbers 1 through 15 shown in FIG. 11. A mark 168, such as red paint, is placed on the top edge of portion 164 of the pusher 142. The mark is visible through the top surface 152 of the housing 149. The numbered indicia are positioned in such a way that the alignment of the mark 168 with the indicia indicates the number of clips remaining in the cartridge.

Returning now to FIG. 8, the instrument includes a jaw housing 180 which is generally an elongated U-shaped channel having a bottom 182 FIG. 2) and parallel side walls 184 and 186. The distal length of the closure member 100, sits in the bottom of the channel with the jaw member 107, driver element 62 and cartridge assembly 130 on top of the closure member in that order. Inwardly directed tabs 188 located across from one another on side walls 184 and 186 engage slots 190 in the sides of plug 130 to hold the distal half of the instrument together.

A flexible clip stop pawl member 192 is formed out of the bottom of the distal end of the jaw housing. It extends from the longitudinal center of the bottom of the jaw housing distally past the distal ends of the side walls 184 and 186. The pawl member is connected to the bottom of the jaw housing only at this proximal end. It is bent upwardly out of the plane of the bottom of the jaw housing a first time to form a first camming surface 194 which terminates in a straight section 195 which in turn is bent upwardly again at 196 to terminate in a clip stop end portion 198. See FIGS. 11-13.

Referring now to FIGS. 11 through 13, FIG. 11 shows the distal portion of the instrument in enlarged cross-section with the instrument at rest. A clip 135a is located between the jaws 112 and 114 with only jaw 112 shown in FIG. 11. The distal end of the feeder member 134 extends beyond the distal end of cartridge 130 with the clip engaging end surface 136 positioned just behind the clip. This keeps the clip from sliding backward out of the jaws. The clip engaging inner surfaces of the jaws are grooved at 200 from near the distal tip, but not as far as the tip, to the proximal most end of the jaws. The clip is captured within the grooves 200 making it more stable. The rear most portion 202 of the grooves are flared and intersect the clip feeding path from the cartridge. In FIG. 11 the distal end of the feeder member 134 which is flexible has engaged the grooves as well as the clip. The next clip to be applied, 135b, is firmly positioned within the cartridge squeezed on top and bottom between the inner surface of the cartridge top 149 and the feeder 134. The legs of clip 135c are pushing the web of clip 135b against center delta portion 158 while the legs of clip 135b engage the distal ramp surfaces 204 formed by taper 156 in the housing 149. Clip 135c is being pressed distally by the clip behind or, if it is the last clip, by the pusher 142 as shown in FIG. 11. Until the feeder member 134 is retracted proximally, the clips 135b and 135c cannot move. Note that the jaw member is shown passing through opening 106 in the distal end 101 of the closure member 100. The driver link 62 is shown at its distal most position just proximal of the distal end 101 of the closure base 100 when the instrument is at rest. Post 50 of yoke 44 is located distally of the vertex 94 of cam track 90 in the handle housing 12 and the ring handles are spread apart to their maximum.

The cartridge bottom 132 is shown on top of the driver link 62 and the clip stop end portion 198 of jaw housing 180 engages the underside of the legs of the clip 135a.

Looking now at FIG. 12, the ring handles have been squeezed causing the links 34 and 36 to push the yoke 44 proximally which in turn pulls the driver link 62 proximally. Since the post 138 of the feeder member 134 is coupled to the hole 140 in the drive link 62 through slot 139 in the bottom 132 of the cartridge (FIG. 9), the feeder member 134 will also move proximally. When the feeder member moves out of the jaws into the cartridge, the end 198 of the pawl member 192 moves in between the jaws to act as a clip stop preventing the clip 135a from moving backwards. The end 198 is biased into this position by the curved portion 196. Once the feeder member pulls back proximally past the web of clip 135b, clip 135b is free to translate into the clip feed path in front of the feeder member being forced there by pusher 142 because of spring 148. The web of the clip moves down against the center ramp surface 208 formed by the delta shape of the distal end of the cut out 158 while the legs move down against the ramp surface 204. The ramp surface 208 extends down into the feed path between the legs of the clip against the inner surface of the web. This helps to stabilize the clip 135b and keep it from moving during the remainder of the crimping cycle. At this point if the feeder 134 were allowed to move forward it would force clip 135b into the jaws behind the uncrimped clip 135a causing a double feed problem. This is prevented because the post 50 on ratchet yoke 44 has come to rest in cut out 96 in the cam track preventing distal movement of the driver link 62 if the ring handles were released. As shown in FIG. 12, up to this point the driver link 62 and 20 feeder 134 have moved proximally, clips 135b and c have moved along with pusher 142 and the clip stop 198 has moved in between the jaws behind clip 135a.

Referring now to FIGS. 11, 12 and 8, as the ring handles are squeezed closer together, the driver link 62 continues to move proximally. The driver link 62 includes a bent down tab 210 in the center of the driver link 62 which moves within an elongated slot 212 in the jaw member 107. The jaw member also includes elongated slot 214 located proximally of slot 212. Slot 214 receives post 138 from feeder 134 through the hole 140 in the driver link 62. The slots in the jaw member 107 allow the driver link and feeder member 134 to move between the positions shown in FIGS. 11 and 12 in either direction without moving the jaw member 107 or cartridge. Driver link 62 includes an elongated slot 216 in its distal portion to accommodate the tab 120 from the closure member when the driver link 62 moves relative to the jaw member 107. The jaw member includes a slot 220 to accommodate tab 153 from the cartridge assembly which tab passes within the slot 162 in the side of the driver link. The slot 162 is larger than the slot 220 to accommodate movement of the driver link relative to both the jaw member 107 coupled to cartridge assembly 130 by tab 153.

As the ring handles are squeezed, the distal end of slot 162 in the driver link 62, engages tab 153 on the cartridge assembly and the bent tab 210 on the driver link engages the proximal end of slot 212 in the jaw member 107. As the driver link continues to move proximally, the jaw member 107 and cartridge assembly 130, including the jaw housing 180, move proximally relative to the closure member 100 which remains fixed relative to the instrument housing. The relative movement is shown in FIG. 13. As the jaw member 107 moves proximally, the curved camming surfaces 116 and 118 at the rear of the jaws 112 and 114, respectively, engage the distal end 101 of the closure member inside the vertical portion of the opening 106. This forces the jaws to move toward one another thereby crimping the legs of the clip 135a closed. Just before the camming surfaces engage distal end 101 of closure member 100, however, the camming surface 194 of the pawl member 192 engages the rounded bottom of the distal end 101 to move the pawl member 192 downward. This removes the portion 198 from between the jaws 112 and 114 allowing them to close. This is clearly shown in FIG. 13. The clips 135b and 135c have not yet moved nor has feeder member 134.

The post 50 on ratchet yoke 44 has moved out of the cut out 96 into the slot 92 when the instrument is in the state shown in FIG. 13. The ring handles have been squeezed as far as they can be. Now as the ring handles are released, the compression spring 83 forces the driver link 62 distally. The biasing spring 127 pulls the jaw member 107 distally with the driver link and, through the slot 220 and tab 153, the jaw member pulls the cartridge forward as well. Hence, initially all elements move together until the rear 111 of slot 110 in the jaw member encounters the tab 120 in the closure member then the cartridge and jaw member stop moving. At this point, the instrument has returned to the state shown in FIG. 12 but without a clip present between the jaws. The driver link 62 will continue to move until the tab 210 hits the distal portion of slot 212 in the jaw member. As the driver link 62 continues to move distally relative to the cartridge and jaws, the feeder member 134 also moves engaging the rear of clip 135b. The web of clip 135b forces the bottom of the distal end of the delta member up until the clip clears the distal end of the delta member. The bottom of the delta member then slides in the slot 230 in the center of the feeder.

At the clip 135b moves forward, its legs encounter the flared groove portion 202 in the inner clip crimping surfaces of the jaws. The grooves guide the feeder and clip into the center of the jaws aligned with the jaw angle. The clip moves the clip stop end portion 198 of the pawl member 192 out of the way and the instrument has returned to the position shown in FIG. 11.

What is claimed is:

1. An instrument for applying hemostatic clips to tissue comprising:
   a body;
   a jaw means for retaining, holding and crimping a hemostatic clip, including a pair of spaced apart jaws at the end of said body, the jaws being movable relative to each other between an open position and a closed position in their common plane to deform the clip positioned between said pair of jaws; means for camming the jaws closed including first cam surface means associated with the jaws and coupled to said jaw means and second cam surface means affixed to the body and located proximally of the first cam surface means, and means for moving the jaw means and first cam surface means proximally into engagement with the second cam surface means to cause the jaws to move towards one another in their common plane to deform the clip;
   a cartridge assembly coupled to said jaw means for movement therewith, said cartridge assembly including means for storing a plurality of hemostatic clips in a column;
   dispensing means for selectively removing a hemostatic clip from said column in sequential fashion, said dispensing means comprising feed means for transferring a clip from said column to said jaws; and
   a jaw housing affixed to said cartridge assembly, the combined unit formed by said jaw housing and cartridge assembly enclosing said second cam surface means and being graspable by a user of the instrument and movable relative to said body and second cam surface means;
   said instrument further comprising:
   actuating and sequencing means for sequentially actuating the means for feeding and the means for camming including lever means movable between a first open position and a second closed position, movement of said lever means from said first open position to said second closed position causing the camming means to move the jaws towards each other to close the clip.

2. The instrument of claim 1 wherein movement of said lever means from said first open position to said second closed position first causes the feeding means to withdraw from said jaws and then causes the camming means to move.

3. The instrument of claim 2 wherein said instrument further comprises:
   means for preventing said clip from slipping within said jaws after said feed means has retracted but before said camming means has been activated, said preventing means including a flexible pawl member integrally formed with and extending from the distal end of said jaw housing along the longitudinal axis thereof, and having a distal end positioned between said jaws behind a clip held by said jaws when said feeding means is withdrawn, and a camming surface for engagement with said distal end of said body to move said pawl member distal end from between said jaws when said camming means is activated whereby said jaws are free to move relative to one another.

4. The instrument of claim 1 wherein said activating and sequencing means comprises a single driver link coupled between said lever means and said jaw means and cartridge assembly, said driver link and said feed means being moved proximally when said lever means moves from said first open position to said second closed position.

5. The instrument of claim 4 wherein said first cam surface means comprises a cam surface extending laterally outwardly from each of said jaws and wherein said second cam surface means comprises a slot in the body distal end, the profile of said cam surfaces being such as to cause the jaws to close more quickly at the beginning of the closure of the jaws and more slowly at the end.

6. The instrument of claim 1 wherein said cartridge assembly comprises a pre-assembled cartridge assembly comprising:
   top and bottom housing portions;
   feeding means slidable along said housing bottom;
   an array of hemostatic clips directly supported by said feeding means and slidable thereon;
   said dispensing means including a pusher means for pushing said array of clips to the distal end of said cartridge assembly, and means for moving the distal most clip to a feeding path in front of said feeding means when said feeding means is retracted a predetermined distance from said jaws.

7. The instrument of claim 6 where said driver link comprises a flat elongated member and is coupled to said feeding means on one side and to said jaw means on said other side.

8. The instrument of claim 7 wherein said instrument comprises a jaw housing coupled to said cartridge top to encircle a distal portion of aid body, said jaw means and driver link disposed between said jaw housing and said cartridge bottom.

9. The instrument of claim 6 wherein said cartridge assembly comprises a transparent plastic top with indicia placed thereon to indicate the number of clips remaining in said cartridge.

10. The instrument of claim 9 wherein said dispensing means comprises in part a spring biased pusher engaging the proximal most clip in said column, said pusher being visibly highlighted to make the pusher more visible through said transparent top.

11. An instrument for applying hemostatic clips to tissue comprising:
   a body;
   a jaw means for retaining, holding and crimping a hemostatic clip, including a pair of spaced apart jaws at the end of said body, the jaws being movable relative to each other between an open position and a closed position in their common plane to deform the clip positioned between said pair of jaws; means for camming the jaws closed including first cam surface means associated with the jaws and coupled to said jaw means and second cam surface means associated with the body located proximally of the first cam surface means, and means for moving the jaw means and first cam surface means proximally into engagement with the second cam surface means to cause the jaws to move towards one another in their common plane to deform the clip;
   a cartridge assembly coupled to said jaw means for movement therewith including:
   means for storing a plurality of hemostatic clips in a column;
   dispensing means for selectively and automatically dispensing a hemostatic clip from said column in sequential fashion to a feeding path distally of the distal end of the below named feeding means when said feeding means is retracted but before said jaws move from said open position; and
   feeding means for transferring a dispensed clip from said column to said jaws;
   said instrument further comprising:
   actuating and sequencing means for sequentially actuating the means for feeding and the means for camming including lever means movable between a first open position and a second closed position, movement of said lever means from said first open position to said second closed position first causing the feeding means to withdraw from said jaws and then causing the camming means to move the jaws towards each other to close the clip, and movement of said lever means from said second closed position to said first open position causing said jaws to move from said closed position to said open position and subsequently causing said feeding means to feed a new clip to said spaced apart jaws,
   said instrument further comprising means for preventing feeding of another clip to said jaws after said feeding means has been retracted into said cartridge until after said lever means has been moved to said second position, said preventing means comprising a yoke coupled to said lever means for moving proximally with respect to said body when said lever means is moved from said first open position to said second closed position and a cam track associated with the proximal end of said body, said yoke including a cam track follower for engagement with said cam track during movement of said yoke between first and second positions of said lever means, said cam track follower engaging one side of said cam track when said yoke moves proximally and an opposite side of said cam track when said yoke moves distally, said cam track preventing said yoke from moving distally after said feeding means has retracted until said lever means reaches said second position. ,

* * * * *